(12) United States Patent
Belcheva et al.

(10) Patent No.: US 8,968,818 B2
(45) Date of Patent: Mar. 3, 2015

(54) MEDICAL DEVICES HAVING ACTIVATED SURFACES

(75) Inventors: Nadya Belcheva, Hamden, CT (US); Ferass Abuzaina, Shelton, CT (US); Amin Elachchabi, Hamden, CT (US); Mbiya Kapiamba, Cromwell, CT (US); Ahmad Robert Hadba, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 313 days.

(21) Appl. No.: 13/202,373

(22) PCT Filed: Feb. 19, 2010

(86) PCT No.: PCT/US2010/024737
§ 371 (c)(1),
(2), (4) Date: Oct. 26, 2011

(87) PCT Pub. No.: WO2010/096654
PCT Pub. Date: Aug. 26, 2010

(65) Prior Publication Data
US 2012/0046737 A1 Feb. 23, 2012

Related U.S. Application Data

(60) Provisional application No. 61/154,376, filed on Feb. 21, 2009.

(51) Int. Cl.
| A61L 33/06 | (2006.01) |
| A61L 31/14 | (2006.01) |
| C08J 7/14 | (2006.01) |
| C08J 7/12 | (2006.01) |
| A61L 33/04 | (2006.01) |
| A61L 31/14 | (2006.01) |
| A61L 31/04 | (2006.01) |
| A61F 2/06 | (2013.01) |
| A61F 2/50 | (2006.01) |
| A61F 13/00 | (2006.01) |

(52) U.S. Cl.
CPC ............... *A61L 31/14* (2013.01); *A61L 33/06* (2013.01); *A61L 31/04* (2013.01); *C08J 7/12* (2013.01); *C08J 7/14* (2013.01); *A61L 2400/18* (2013.01); *C08J 2300/16* (2013.01)
USPC ......... 427/2.24; 427/2.31; 523/205; 623/1.44

(58) Field of Classification Search
USPC ......... 523/205; 427/2.24, 2.31; 623/144, 1.44
See application file for complete search history.

(56) References Cited

U.S. PATENT DOCUMENTS

| 3,767,085 | A | 10/1973 | Cannon et al. |
| 4,326,532 | A | 4/1982 | Hammar |
| 4,359,049 | A | 11/1982 | Redl et al. |
| 4,464,321 | A | 8/1984 | Pittalis et al. |
| 4,538,920 | A | 9/1985 | Drake |
| 4,753,536 | A | 6/1988 | Spehar et al. |
| 4,839,345 | A | 6/1989 | Doi et al. |
| 4,857,403 | A | 8/1989 | De Lucca et al. |
| 4,880,662 | A | 11/1989 | Habrich et al. |
| 5,021,207 | A | 6/1991 | De Lucca et al. |
| 5,372,585 | A | 12/1994 | Tiefenbrun et al. |
| 5,455,308 | A | 10/1995 | Bastiaansen |
| 5,562,946 | A | 10/1996 | Fofonoff et al. |
| 5,578,662 | A | 11/1996 | Bennett et al. |
| 5,582,955 | A | 12/1996 | Keana et al. |
| 5,612,050 | A | 3/1997 | Rowe et al. |
| 5,804,318 | A | 9/1998 | Pinchuk et al. |
| 5,911,942 | A | 6/1999 | Fofonoff et al. |
| 6,099,563 | A | 8/2000 | Zhong |
| 6,107,365 | A | 8/2000 | Bertozzi et al. |
| 6,107,453 | A | 8/2000 | Zuccato et al. |
| 6,312,725 | B1 | 11/2001 | Wallace et al. |
| 6,342,591 | B1 | 1/2002 | Zamora et al. |
| 6,451,032 | B1 | 9/2002 | Ory et al. |
| 6,461,665 | B1 * | 10/2002 | Scholander .................. 427/2.24 |
| 6,534,611 | B1 | 3/2003 | Darling et al. |
| 6,552,103 | B1 | 4/2003 | Bertozzi et al. |
| 6,559,132 | B1 * | 5/2003 | Holmer ........................ 514/56 |
| 6,570,040 | B2 | 5/2003 | Saxon et al. |
| 6,576,000 | B2 | 6/2003 | Carrison |
| 6,624,245 | B2 | 9/2003 | Wallace et al. |
| 6,881,766 | B2 | 4/2005 | Hain |
| 6,958,212 | B1 | 10/2005 | Hubbell et al. |
| 7,012,126 | B2 | 3/2006 | Matsuda et al. |
| 7,037,527 | B2 * | 5/2006 | Bide et al. .................... 424/486 |
| 7,105,629 | B2 | 9/2006 | Matsuda et al. |
| 7,122,703 | B2 | 10/2006 | Saxon et al. |
| 7,144,976 | B2 | 12/2006 | Matsuda et al. |

(Continued)

FOREIGN PATENT DOCUMENTS

| BE | 1008260 A6 | 2/1996 |
| DE | 10106230 A1 | 8/2002 |

(Continued)

OTHER PUBLICATIONS

Q. Shi, et al., "The Immobolization of Proteins on Biodegradable Polymer Fibers via Click Chemistry", Biomaterials, 29, (2008), pp. 1118-1126.

Jérôme, et al., "Recent Advances in the Synthesis of Alipathic Polyesters Ring-Opening Polymerization", Advanced Drug Delivery Reviews, 60, (2008), pp. 1056-1076.

Zhang, et al., "2-Azido-2-deoxycellulose: Synthesis and 1,3-Dipolar Cycloaddition", Helvetica Chimica Acta, vol. 91, pp. 608-617 (2008).

R. Riva, et al., "Contribution of "Click Chemistry" to the Synthesis of Antimicrobial Alipathic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

(Continued)

*Primary Examiner* — Tae H Yoon

(57) ABSTRACT

Implantable biocompatible polymeric medical devices include a substrate with an acid or base-modified surface which is subsequently modified to include click reactive members.

6 Claims, No Drawings

(56) References Cited

U.S. PATENT DOCUMENTS

| | | | |
|---|---|---|---|
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,560,588 B2 | 7/2009 | Breitenkamp et al. | |
| 7,618,944 B2 | 11/2009 | Breitenkamp et al. | |
| 7,638,558 B2 | 12/2009 | Breitenkamp et al. | |
| 7,667,012 B2 | 2/2010 | Saxon et al. | |
| 7,795,355 B2 | 9/2010 | Matyjaszewski et al. | |
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 8,034,396 B2 | 10/2011 | Kapiamba et al. | |
| 8,182,890 B2 * | 5/2012 | Zheng et al. | 428/36.9 |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0135238 A1 | 7/2003 | Milbocker | |
| 2003/0162903 A1 | 8/2003 | Day | |
| 2003/0199084 A1 | 10/2003 | Saxon et al. | |
| 2003/0205454 A1 | 11/2003 | Hlavinka et al. | |
| 2003/0216524 A1 | 11/2003 | Bide et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2004/0249438 A1 | 12/2004 | Lefranc et al. | |
| 2005/0032081 A1 | 2/2005 | Ju et al. | |
| 2005/0038472 A1 | 2/2005 | Furst | |
| 2005/0060028 A1 * | 3/2005 | Horres et al. | 623/1.38 |
| 2005/0148032 A1 | 7/2005 | Saxon et al. | |
| 2005/0222427 A1 | 10/2005 | Sharpless et al. | |
| 2005/0233389 A1 | 10/2005 | Ting et al. | |
| 2005/0244453 A1 | 11/2005 | Stucke et al. | |
| 2006/0018948 A1 | 1/2006 | Guire et al. | |
| 2006/0036022 A1 | 2/2006 | Callaghan et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0142404 A1 | 6/2006 | Berge et al. | |
| 2006/0147963 A1 | 7/2006 | Barone et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0140966 A1 | 6/2007 | Chang et al. | |
| 2007/0178133 A1 | 8/2007 | Rolland | |
| 2007/0178448 A1 | 8/2007 | Tsao et al. | |
| 2007/0190597 A1 | 8/2007 | Agnew et al. | |
| 2007/0212267 A1 | 9/2007 | Organ et al. | |
| 2007/0244265 A1 | 10/2007 | Matyjaszewski et al. | |
| 2007/0244296 A1 | 10/2007 | Tomalia et al. | |
| 2007/0249014 A1 | 10/2007 | Agnew et al. | |
| 2007/0254006 A1 | 11/2007 | Loose et al. | |
| 2007/0258889 A1 | 11/2007 | Douglas et al. | |
| 2007/0269369 A1 | 11/2007 | Gegg et al. | |
| 2007/0272122 A1 | 11/2007 | Lahann et al. | |
| 2007/0275387 A1 | 11/2007 | Ju | |
| 2007/0298006 A1 | 12/2007 | Tomalia et al. | |
| 2008/0015138 A1 | 1/2008 | Hamilton et al. | |
| 2008/0021486 A1 | 1/2008 | Oyola et al. | |
| 2008/0035243 A1 | 2/2008 | Breitenkamp et al. | |
| 2008/0038472 A1 | 2/2008 | Suzuki et al. | |
| 2008/0045686 A1 | 2/2008 | Meagher et al. | |
| 2008/0050731 A1 | 2/2008 | Agnew et al. | |
| 2008/0051562 A1 | 2/2008 | Chaikof et al. | |
| 2008/0103564 A1 | 5/2008 | Burkinshaw et al. | |
| 2008/0121657 A1 | 5/2008 | Voegele et al. | |
| 2008/0138317 A1 | 6/2008 | Fung | |
| 2008/0160017 A1 | 7/2008 | Baker et al. | |
| 2008/0166363 A1 | 7/2008 | Govindan et al. | |
| 2008/0171067 A1 | 7/2008 | Govindan et al. | |
| 2008/0187956 A1 | 8/2008 | Carrico et al. | |
| 2008/0199736 A1 | 8/2008 | Gadeken et al. | |
| 2008/0200628 A1 | 8/2008 | Gadeken et al. | |
| 2008/0207913 A1 | 8/2008 | Breitenkamp et al. | |
| 2008/0214436 A1 | 9/2008 | Yu et al. | |
| 2008/0214801 A1 | 9/2008 | Saxon et al. | |
| 2008/0214831 A1 | 9/2008 | Sharpless et al. | |
| 2008/0221043 A1 | 9/2008 | Harth et al. | |
| 2008/0241856 A1 | 10/2008 | Wong et al. | |
| 2008/0241892 A1 | 10/2008 | Roitman et al. | |
| 2008/0242171 A1 | 10/2008 | Huang et al. | |
| 2008/0248126 A1 | 10/2008 | Cheng et al. | |
| 2008/0267878 A1 | 10/2008 | Robillard et al. | |
| 2008/0283572 A1 | 11/2008 | Boyden et al. | |
| 2008/0311412 A1 | 12/2008 | Fokin et al. | |
| 2008/0317861 A1 | 12/2008 | Guan | |
| 2009/0012457 A1 | 1/2009 | Childers et al. | |
| 2009/0018646 A1 | 1/2009 | Zhao | |
| 2009/0024086 A1 | 1/2009 | Zhang et al. | |
| 2009/0024096 A1 | 1/2009 | Hai et al. | |
| 2009/0027603 A1 | 1/2009 | Samulski et al. | |
| 2009/0038701 A1 | 2/2009 | Delmotte | |
| 2009/0053139 A1 | 2/2009 | Shi et al. | |
| 2009/0054619 A1 | 2/2009 | Baker et al. | |
| 2009/0061010 A1 | 3/2009 | Zale et al. | |
| 2009/0069561 A1 | 3/2009 | Fokin et al. | |
| 2009/0082224 A1 | 3/2009 | Haddleton et al. | |
| 2009/0099108 A1 | 4/2009 | Jones | |
| 2009/0124534 A1 | 5/2009 | Reineke et al. | |
| 2009/0137424 A1 | 5/2009 | Tsao et al. | |
| 2009/0181402 A1 | 7/2009 | Finn et al. | |
| 2009/0182151 A1 | 7/2009 | Wu et al. | |
| 2009/0202433 A1 | 8/2009 | Chang et al. | |
| 2009/0203131 A1 | 8/2009 | Reineke et al. | |
| 2009/0214755 A1 | 8/2009 | Armani et al. | |
| 2009/0220607 A1 | 9/2009 | Kiser et al. | |
| 2009/0240030 A1 | 9/2009 | Ju et al. | |
| 2009/0247651 A1 | 10/2009 | Kapiamba et al. | |
| 2009/0250588 A1 | 10/2009 | Robeson et al. | |
| 2009/0253609 A1 | 10/2009 | Fleury et al. | |
| 2009/0259016 A1 | 10/2009 | Johnson et al. | |
| 2009/0263468 A1 | 10/2009 | McAnulty et al. | |
| 2009/0269277 A1 | 10/2009 | Chang et al. | |
| 2009/0281250 A1 | 11/2009 | DeSimone et al. | |
| 2009/0297609 A1 | 12/2009 | Shoichet et al. | |
| 2009/0306310 A1 | 12/2009 | Wu et al. | |
| 2009/0306335 A1 * | 12/2009 | Harth et al. | 528/403 |
| 2009/0312363 A1 | 12/2009 | Bradner et al. | |
| 2009/0325292 A1 | 12/2009 | Baker et al. | |
| 2010/0011472 A1 | 1/2010 | Hugel et al. | |
| 2010/0015046 A1 | 1/2010 | Govindan et al. | |
| 2010/0021391 A1 | 1/2010 | Douglas et al. | |
| 2010/0034862 A1 | 2/2010 | Laronde et al. | |
| 2010/0047258 A1 | 2/2010 | Wang et al. | |
| 2010/0048738 A1 | 2/2010 | Fleury et al. | |
| 2010/0069578 A1 | 3/2010 | Faust et al. | |
| 2010/0098640 A1 | 4/2010 | Cohen et al. | |
| 2010/0104589 A1 | 4/2010 | Govindan et al. | |
| 2010/0121022 A1 | 5/2010 | Musa et al. | |
| 2010/0159508 A1 | 6/2010 | Yang et al. | |
| 2010/0160299 A1 * | 6/2010 | Baker et al. | 514/221 |
| 2010/0247433 A1 | 9/2010 | Tirrell et al. | |
| 2010/0286405 A1 | 11/2010 | Fokin et al. | |
| 2010/0291171 A1 | 11/2010 | Crescenzi et al. | |
| 2010/0303754 A1 | 12/2010 | Turpin et al. | |
| 2011/0008251 A1 | 1/2011 | Chang et al. | |
| 2011/0008404 A1 * | 1/2011 | Lyon et al. | 424/422 |
| 2011/0052696 A1 | 3/2011 | Hult et al. | |
| 2011/0060107 A1 | 3/2011 | Matyjaszewski et al. | |
| 2011/0143435 A1 | 6/2011 | Stayton et al. | |

(56) References Cited

U.S. PATENT DOCUMENTS

| | | |
|---|---|---|
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |

FOREIGN PATENT DOCUMENTS

| | | |
|---|---|---|
| EP | 0490854 B1 | 9/1996 |
| EP | 1790702 A1 | 5/2007 |
| EP | 1795563 A1 | 6/2007 |
| EP | 1975230 A1 | 1/2008 |
| EP | 2014308 A2 | 1/2009 |
| EP | 2090592 A1 | 8/2009 |
| WO | WO 2006/012569 A1 | 2/2006 |
| WO | WO 2007/041394 A2 | 4/2007 |
| WO | WO 2007/121055 A1 | 10/2007 |
| WO | WO 2008/013618 A1 | 1/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2010/095049 A1 | 8/2010 |

OTHER PUBLICATIONS

Codelli, et al., "Second Generation Difluorinated Cyclooctynes for Copper-Free Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (ε-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis- 1,2,3-triazoles", Carbohydrate Research, 343, (2008), 139-144.

Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i +4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization, "Biomacro molecules, 2007, 8(2), pp. 327-330.

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

European Search Report, Application No. 10 74 4359 dated Mar. 13, 2014.

* cited by examiner

MEDICAL DEVICES HAVING ACTIVATED SURFACES

CROSS-REFERENCE TO RELATED APPLICATIONS

This application is a U.S. National Stage Application filed under 35 U.S.C. §371(a) of International Application No. PCT/US2010/024737 filed Feb. 19, 2010, which claims the benefit of and priority to U.S. Provisional Application Ser. No. 61/154,376 filed Feb. 21, 2009, the entire contents of which are incorporated by reference herein.

BACKGROUND

1. Technical Field

The present disclosure relates to surface-activated polymers and to a methods for preparation thereof. Medical devices made from or containing such surface-activated polymers are also described herein.

2. Related Art

Biocompatible and biodegradable materials have been used for the manufacture of prosthetic implants, suture threads, and the like. A relative advantage of these materials is that of eliminating the need for a second surgical intervention to remove the implant. The gradual biodegradability of such materials favors regeneration of the pre-existing tissues. There has been recent interest in using such devices for delivery of bioactive agents.

It would be advantageous to provide reactive functional groups on the surface of such biodegradable medical devices for a variety of purposes.

SUMMARY

Implantable biocompatible polymeric medical devices in accordance with the present disclosure include a substrate with an acid or base-modified surface which is subsequently functionalized to include click reactive members. The substrate of the medical devices described herein may be made from any biocompatible polymer and can be part of any medical device of being implanted at a target location. Acid or base treatment of the substrate may result in chemical modification of the material from which the substrate is made thereby facilitating functionalization of the surface or attachment of a linker compound which can be functionalized with click reactive members.

DETAILED DESCRIPTION OF THE EMBODIMENTS

Implantable biocompatible polymeric medical devices in accordance with the present disclosure include a substrate with an acid or base modified surface which is subsequently functionalized to include click reactive members.

The Polymeric Substrate

The substrate of the medical devices described herein may be made from any biocompatible polymer. The biocompatible polymer may be a homopolymer or a copolymer, including random copolymer, block copolymer, or graft copolymer. The biocompatible polymer may be a linear polymer, a branched polymer, or a dendrimer. The biocompatible polymer may be bioabsorbable or non-absorbable and may be of natural or synthetic origin.

Examples of suitable biodegradable polymers from which the substrate of the medical devices described herein may be made include, but are not limited to polymers such as those made from alpha-hydroxy acids (e.g. lactic acid, glycolic acid, and the like), lactide, glycolide, ε-caprolactone, δ-valerolactone, carbonates (e.g., trimethylene carbonate, tetramethylene carbonate, and the like), dioxanones (e.g., 1,4-dioxanone), 1,dioxepanones (e.g., 1,4-dioxepan-2-one and 1,5-dioxepan-2-one), ethylene glycol, ethylene oxide, esteramides, hydroxy alkanoates (e.g. γ-hydroxyvalerate, β-hydroxypropionate, 3-hydroxybuterate, and the like), poly (ortho esters), tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include collagen, cellulose, poly (amino acids), polysaccharides, hyaluronic acid, gut, copolymers and combinations thereof.

Examples of suitable non-degradable polymers from which the substrate of the medical devices described herein may be made include, but are not limited to fluorinated polymers (e.g. fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyaryletherketone, copolymers and combinations thereof.

The biocompatible polymeric substrate may be fabricated into any desired physical form. The polymeric substrate may be fabricated for example, by spinning, casting, molding or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

The present biocompatible polymeric substrate can be part of any medical device of being implanted at a target location. Some non-limiting examples include monofilaments, multifilaments, surgical meshes, ligatures, sutures, staples, patches, slings, foams, pellicles, films, barriers, stents, catheters, shunts, grafts, coil, inflatable balloon, and the like. The implantable device can be intended for permanent or temporary implantation.

Treatment of the Substrate

Surface activation of the substrate is provided by acid or base hydrolysis.

In embodiments, the process of hydrolysis is conducted in the presence of an aqueous solution of a base or an acid to accelerate surface reaction, inasmuch as excessively long processes of activation can induce a reduction in molecular weight and thus in the mechanical properties of the material. Suitable bases for use in the present hydrolysis processes include, for example, strong alkalis, such as LiOH, Ba(OH)$_2$, Mg(OH)$_2$, NaOH, KOH, Na$_2$CO$_3$, Ca(OH)$_2$ and the weak bases, such as for example NH$_4$OH and the amines such as methylamine, ethylamine, diethylamine and dimethylamine. Acids suitable for surface hydrolysis treatments can be chosen, for example, from among HCl, HClO$_3$, HClO$_4$, H$_2$SO$_3$, H$_2$SO$_4$, H$_3$PO$_3$, H$_3$PO$_4$, HI, HIO$_3$, HBr, lactic acid, glycolic acid.

Surface activation by means of hydrolysis can be conducted at temperatures preferably comprised between 0 degrees Celsius and the material softening temperature or glass transition temperature.

Surface hydrolysis treatment is followed by careful washing to remove all traces of acid or base.

The present surface treatment can generate COONa groups which can be subsequently converted into COOH groups by treatment with strong mineral acids.

Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—CH$_2$—CH$_2$—COOH groups.

Addition of Reactive Members to the Treated Substrate

Once a surface of the substrate is acid or base treated, click reactive functional groups are provided on the surface.

Examples of the types of reactions that are known to have click reactivity include cycloaddition reactions. Cycloaddition reactions can be used to activate the substrates of the present disclosure. These reactions represent highly specific reactant pairs that have a chemoselective nature, meaning that they mainly react with each other and not other functional groups. One example of a cycloaddition reaction is the Huisgen 1,3-dipolar cycloaddition of a dipolarophile with a 1,3 dipolar component that produce five membered (hetero) cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene).

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —SO2Cl and an olefin (R$^1$, R$^2$—C═C—R$^3$, R$^4$), metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, attached functionality may be chosen from acetylene bond, an azido-group, a nitrile group, acetylenic, amino group, phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group including polypeptides, proteins and nucleic acids, to the polymer.

Thus, suitable reactive members that may be applied to the treated substrate include, for example, an amine, sulfate, thiol, hydroxyl, azide, alkyne, alkene, carboxyl groups aldehyde groups, sulfone groups, vinylsulfone groups, isocyanate groups, acid anhydride groups, epoxide groups, aziridine groups, episulfide groups, groups such as —CO$_2$N(COCH$_2$)$_2$, —CO$_2$N(COCH$_2$)$_2$, —CO$_2$H, —CHO, —CHOCH$_2$, —N═C═O, —SO$_2$CH═CH$_2$, —N(COCH)$_2$, —S—S—(C$_5$H$_4$N) and groups of the following structures wherein X is halogen and R is hydrogen or C$_1$ to C$_4$ alkyl:

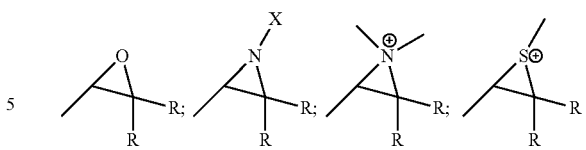

The treated substrate can be provided with click reactive members using any variety of suitable chemical processes. Those skilled in the art reading this disclosure will readily envision chemical reactions for activating treated substrate to render them suitable for use in the presently described devices/methods.

For example, in embodiments, the acid or base treated substrate is functionalized with a halogen group to provide a reactive site at which a click reactive member can be attached. The halogenated sites on the surface of the treated substrate can be functionalized with a click reactive member, for example, by converting pendant chlorides or iodides on the core into azides by reaction with sodium azide. See, R. Riva et al., *Polymer* 49, pages 2023-2028 (2008) for a description of suitable reaction conditions.

Alternatively, the polymer or copolymer backbone may be halogenated using methods similar to those described by Nottelet et al., *Biomaterials*, 27, pages 4948-4954 (2006). Once halogenated, the backbone can be functionalized with a click reactive functionality by reacting it with a hydroxyacid under condition described by Shi et al. Biomaterials, 29, pages 1118-1126 (2008) followed by reaction with sodium azide. The halogen can also be converted directly to the alkyne by reacting it with an alcoholic alkine suck as propargyl alcohol.

Uses of Medical Devices Having an Activated Surface

Medical devices having an activated surface in accordance with the present disclosure can be used for a variety of purposes. For example, in embodiments they may be used for drug delivery. In such embodiments, the drug to be delivered is functionalized with one or more reactive member that are complementary to the reactive members provided on the surface of the substrate. By "complementary" it is meant that the reactive members on the drug to be delivered are able to interact with the reactive members provided on the surface of the substrate to covalently bond the drug to be delivered to the surface activated substrate.

In other embodiments, the medical device having an activated surface in accordance with the present disclosure can be attached to biological tissue by functionalizing tissue with one or more reactive member that are complementary to the reactive members provided on the surface of the substrate. Biological tissue can be provided with reactive member that are complementary to the reactive members provided on the surface of the substrate by conjugation of such groups to various components of tissue such as proteins, lipids, oligosaccharides, oligonucleotides, glycans, including glycosaminoglycans. In embodiments, the complementary groups are attached directly to components of the tissue. In other embodiments, the complementary groups are attached to components of the tissue via a linker. In either case, situating the complementary groups on the tissue can be accomplished by suspending the reactive member in a solution or suspension and applying the solution or suspension to the tissue such that the reactive member binds to a target. The solution or suspension may be poured, sprayed or painted onto the tissue, whereupon the reactive members are incorporated into the tissue.

Those skilled in the art reading this disclosure will readily envision other uses for the activated medical devices described herein.

It will be understood that various modifications may be made to the embodiments disclosed herein. Therefore, the above description should not be construed as limiting, but merely as exemplifications within the scope and spirit of the claims appended hereto.

What claimed is:

1. A method of preparing a medical device having an activated surface, the method comprising:
   base-treating at least a portion of a surface of a medical device; and
   attaching one or more click reactive members to the base-treated surface of the medical device, wherein the click reactive members are selected from the group consisting of thiols, azides, alkynes, and alkenes.

2. The method according to claim 1, wherein the base is selected from the group consisting of LiOH, $Ba(OH)_2$, $Mg(OH)_2$, NaOH, KOH, $Na_2CO_3$, $Ca(OH)_2$, and $NH_4OH$.

3. The method according to claim 1, wherein the medical device is selected from the group consisting of monofilament sutures, multifilament sutures, surgical meshes, ligatures, staples, slings, patches, foams, pellicles, films, barriers, stents, catheters, and inflatable balloons.

4. The method according to claim 1, wherein the click reactive members are selected from the group consisting of azides and alkynes.

5. The method according to claim 1, wherein the click reactive members are selected from the group consisting of thiols and alkenes.

6. The method according to claim 1, wherein the medical device is a surgical mesh.

* * * * *